United States Patent [19]

Yamaguchi et al.

[11] 4,059,544

[45] Nov. 22, 1977

[54] ACTIVE MATERIAL COMPOSITIONS WITH POROUS PROTECTIVE SHEATH AND METHOD FOR PREPARING

[75] Inventors: Yoshinobu Yamaguchi; Nanahiko Kitano, both of Nagoya; Yoshihisa Watanabe; Makoto Imanari, both of Ami, all of Japan

[73] Assignees: Fujimi Kenmazai Kogyo Kabushiki Kaisha; Mitsubishi Petrochemical Co., Ltd., both of Japan

[21] Appl. No.: 647,558

[22] Filed: Jan. 8, 1976

Related U.S. Application Data

[63] Continuation of Ser. No. 386,294, Aug. 7, 1973, abandoned.

[30] Foreign Application Priority Data

Aug. 10, 1972   Japan ................................. 47-80252

[51] Int. Cl.$^2$ ..................... B01J 23/34; B01J 35/02

[52] U.S. Cl. ............................. 252/471; 252/477 R; 106/41; 427/215; 427/226

[58] Field of Search ............ 252/471, 477 R; 106/41, 106/48, 122; 428/403, 404; 423/213.2; 427/215, 226

[56] References Cited

U.S. PATENT DOCUMENTS

| | | | |
|---|---|---|---|
| 3,030,300 | 4/1962 | Flanders et al. | 252/477 R |
| 3,145,183 | 8/1964 | Fisher | 252/477 R |
| 3,259,454 | 7/1966 | Michalko | 423/213.5 |
| 3,806,466 | 4/1974 | Bird et al. | 252/422 |

*Primary Examiner*—W. J. Shine
*Attorney, Agent, or Firm*—Robert E. Burns; Emmanuel J. Lobato; Bruce L. Adams

[57] ABSTRACT

A particulate composition composed of a core of active material and a protective sheath having communicating micro pores to permit access of reactants to the active materials is described as well as a method for preparing same.

13 Claims, No Drawings

ACTIVE MATERIAL COMPOSITIONS WITH POROUS PROTECTIVE SHEATH AND METHOD FOR PREPARING

This is a continuation, of application Ser. No. 386,294, filed Aug. 7, 1973; now abandoned.

BACKGROUND OF THE INVENTION

1. Field of the Invention

This invention relates to a novel active material-protecting structural compositions which protect an active material core with a sheath and more particularly to such compositions where said active material is either catalysts or adsorbent.

2. Description of the Prior Art

Heretofore, an active material e.g. catalyst, adsorbing agent etc. to be used in vapor phase or liquid phase reactions has been used in a form of powder, or granules prepared of the material itself or admixed of a binder, or adsorbed on a supporting carrier. However, when the active material is used in power form, especially in vapor phase reactions, it requires special design to maintain the powder in a fluid condition. Considerable loss is caused by crushing the powder in fine particles. When the active material is used in liquid phase reactions, separation of the powder from the liquid, is troublesome and continuous operation is difficult. When the active material e.g. catalyst, or adsorbing material is used in the form of granules, some of the disadvantages are eliminated. However, when the active material is granulated, there are certain other drawbacks including a decrease of activity of the material, catalytic or adsorbing activity or low crush strength, impact strength or abrasion strength of the granules. Even though the granules have enough strength at the beginning of their use, the strength gradually or rapidly decreases. during use and continued operations become difficult because of powdering or other forms of decrepitation.

Moreover, when a carrier is used, the active material is often removed from the carrier, and the resultant decreased activity is difficult to overcome.

It is also difficult to increase the ratio of the active ingredient to support while maintaining the proper activity.

It is quite important, in industrial and practical cases using the active material, to overcome the disadvantages caused by powdering of the granules of active materials.

SUMMARY OF THE INVENTION

It is an object of this invention to provide an active material-protecting structural composition having high crush strength, impact strength, abrasion strength to overcome the industrial and practical problems caused by powdering or crushing of ordinary granules of active material.

This object of the invention is achieved by structurally strong particulate composition for active materials comprising a core and a microporous sheath surrounding said core, said core comprising the active material, and said microporous sheath comprising a solid strengthening enclosing structure for said core and having an open porous structure whereby passageways are provided for access between said core and the space surrounding said particulate composition.

It is another object of this invention to provide an active material-projecting structural sheathed core composition wherein the sheath is not destroyed by volume changes of the active material caused by heating or by the chemical reaction. This object is achieved by a sheathed core composition wherein the core is separated from said microporous sheath by a space. It is the other object of this invention to provide an active material-protecting structural composition having high crush strength, impact strength and abrasion strength wherein the active material is a catalyst, as for example the manganese oxide or preparing alkylphenols from phenol and methanol.

It is the other object of this invention to provide an active material-protecting structural composition wherein the active material is an adsorbing agent such as activated carbon, activated alumina, silica gels, molecular sieves, ion-exchanges etc. and/or imparts a desirable adsorbing activity.

The active material-protecting structural composition of this invention is composed of a core of active material and a structurally strong sheath having communicating mirco pores which surrounds the functional material.

This invention includes the method for preparing such structurally protecting compositions.

DETAILED DESCRIPTION OF PREFERRED EMBODIMENTS

The active materials of this invention may be any active ingredients e.g. catalyst, adsorbing agent etc. or mixtures of at least one active ingredient and inert materials or an active ingredient supported upon a carrier or mixture of such active materials. The active material-protecting structural composition is prepared by granulating or subdividing into cores the active material and coating the cores with a sheath material and sintering or otherwise cohering the coating product to form the sheath having micropores communicating externally from the core to provide access thereto of the reaction media. It is possible to prepare the active material-protecting structural composition with the active material having a very large surface area by mixing the active material with a combustible organic powder, forming cores thereof coating the cores with the sheath material and then heating to burn the combustible organic powder to leave communicating voids in said cores.

It is also possible to form a space between the core and the sheath by coating the core with a fugative material such as a combustible organic powder or soluble material on the cores of the active material and then removing the fugitive material, in the sintering in the case of the organic material or by solvent extraction of the soluble material.

Various powdery or granular catalyst, or adsorbing agents etc. can be used as active materials. It is possible to use effectively in stable condition, an active material which is effectively in stable condition, an active material which is easily mechanically or chemically disintegrated during use or regeneration of the catalyst in air, such as manganese oxide commonly used for preparing alkylphenols from phenol and methanol; or for active materials which are easily scattered, such as activated carbon; or for active materials which have poor strength, such as molecular seives, silica gels etc.

The term "active material" as used herein can be a mixture of two or more active material.

The active material can be supported by a carrier and or diluent as when platinum, palladium or the other expensive catalysts are used as active materials.

In accordance with this invention, it is also possible that carriers having relatively low strength can be used as catalyst supports.

The combustible organic materials which may be used for forming porous cores or the spaces between the core and the sheath, can be carbohydrates such as walnut husk powder, fibers, sawdust, cellulose, etc.; and combustible polymers such as polyolefins, polystyrene, etc.

Such combustible organic materials are preferably materials which vaporize or burn at or below sintering temperatures used for forming the sheath.

It is possible to add an inorganic solid which is soluble in water, acid or alkali or other solvents, or sublimeable material, e.g. camphor, instead of the combustible organic material.

The space-forming material can be used for forming the communicating micro pores in and through the sheath. Especially suitable for use are micro-crystalline cellulose, and derivatives of wheat flour, cornstarch, etc.

The sheath materials may be such inorganic powders as fused alumina, silicon carbide, alumina, silica, zirconia etc.; glass powders such as sodium glass, lead glass, borosilicate glass, etc.; metal powders such as iron, aluminum, copper, tin, lead, zinc; alloy powders such as gun-metal, stainless steel etc.; magnesium oxide; cements such as PORTLAND cement, alumina cement etc. Generally fused inorganic salts, oxides, cements of a crystalline or amorphous nature or even pure powdered metals may be used.

It is also possible to use organic polymers. However, when polymers are used the sheath is formed by adhering, cohering bonding or foaming or polymerizing the polymer without using sintering temperatures.

It is possible to use in or as the sheath-forming material, some materials having catalytic or adsorbing activity. For example, when magnesium oxide is used as the sheath material in the preparation of catalysts for preparing alkylphenol, the magnesium oxide itself imparts some catalytic activity Certain sheath materials can easily be sintered, bonded, or cured after coating the cores and then heating. Such materials include copper powder, glass powder, alumina cement, portland cement etc. Most other sheath materials are hard to sinter or bond to themselves and it is preferable to add a binder thereto. The binder is melted or softened by heating to sinter or to bond the sheath material powder. Such binders include clay, kaolin, feldspar, glass powder, etc. It is preferable to add a binder for sintering, bonding or curing the sheath material powder. Temperatures for the sintering, melting or curing range from about 400° to 1400° C.

It is possible to form pores in the sheath by mixing a combustible or vaporizable organic material; such as walnut husk powder, fibers, sawdust, camphor, etc.; and burning or vaporizing it during the sintering.

It is also possible to form pores in the sheath by mixing inorganic or organic powders or fibers which are soluble in acid, alkali or solvents, then forming the sheath and then dissolving out the inorganic power or fibers to leave voids in the form of communicating open pores.

It is preferred that the sheath have the following properties. 1. The sheath should have strength sufficient to prevent crushing by impact or abrasion during normal use. When a crush strength is measured by the Kiya type hardness tester*, the crush strength is preferred to be higher than 3 kg, especially higher than 7 kg. The crush strength of the sheath should be higher than the durable strength for each intended use.

*Measures crushing strength wherein the sample is placed on a balance and pressed to measure the weight required for compression fracture. The unit is Kg.;

2. The sheath should have a plurality of pores of a microscopic nature communicating from outside to the core. Such micro pores are formed by sintering the sheath material with the combustible organic material and like, as stated above, and should not be closed pores or single cells such as in porcelain, but should communicate with each other so as to permit ready passage of gaseous or liquid molecules to and from the other surface of the sheath and the core of the active material. The diameter of the communicating pores, measured by using the porosimeter, is usually 0.05 - 1000 $\mu$ preferably 0.5 - 500 $\mu$ and optimally 1 - 100 $\mu$ and should be of such form and diameter that the active material is kept within the sheath.

It is preferable to have the micro pores as numerous and large as possible within the above conditions. An apparent porosity range that is useful measured by the JIS-R 2205 (1955), is usually in a range of 20–70% preferably 30–65%; the pore volume, measured by the porosimeter, usually in a range of 0.01–0.7 cc/g preferably 0.02–0.6 cc/g.

The thickness of the sheath is dependent upon the strength required of the composition and the degree of porosity. When the thickness of the sheath is increased, the strength is also increased. However the content of the active material in the total composite is relatively decreased, and the flow resistance of the reactants to the active material, is also increased. Accordingly, it is preferred to select the thickness of the sheath providing a desirable strength. A ratio of the thickness of the sheath to the inner diameter of the sheath containing the active material, is usually in a range of 5–100%, preferably 6–50%, especially 8–20%.

The type and amount of the active material, the type and amount of the sheath material, the type and amount of binder, the thickness of the sheath, the particle size, and the ratio of the active material to the sheath the porosity of the sheath, pore diameter, and pore volume can be selected as desired within the above limits to provide the useful compositions according to this invention.

When the active material is relatively inexpensive material such as active carbon, maganese oxide, etc. which can be granulated without using a carrier, the proportion of active ingredient in this particular composition of this invention can be quite high.

When the active material is expensive, and is used with a carrier, an amount of the active ingredient of the active material to total composition weight can be quite small. Because of the structurally protective sheath, the carrier can be an easily powdered or crushable material which otherwise would not be useful.

The sheath for protecting the active material, should have a plurality of communicating-fine pores and should have high crush strength, impact strength and abrasion strength. The thickness of the sheath can be adjusted depending upon the required strength. The strength is dependent upon and results from the bonding forces of the sheath material.

When the coherance or bonding is formed by sintering, especially with high bonding force, it is possible to obtain high strength, even with high porosity.

When the strength of the sheath is high, it is possible to increase the ratio of the active material to the sheath and to decrease the thickness of the sheath.

The diameter of the particulate material of the composition according to this invention is dependent upon the conditions of intended use including use in packing towers, in fluidized bed reactors and is usually in a range of 0.5 to 250 mm. but preferably in the range of 1 to 25 mm.

The active material can be in the form of a powdery core maintained within and by the sheath.

When a space is formed between a solid incompressible core and the sheath, the sheath is not cracked, ruptured or broken by the thermal expansion of the active material. When a catalyst of manganese oxide is used, a volume change occurs during air regeneration which would normally rupture the sheath. However, when a space is formed between the core and the sheath, the life of the particulate composition according to this invention survives repeated regeneration.

In general, when the volume changes of the active material caused by heat or chemical reactions, is high, it is desirable and useful to form a space between the core and the scheath.

The active material can be restricted to the core but also the same or different active material can be added to the sheath structure.

In general, the addition of the active material to the sheath itself, can be achieved by impregnating the particulate composition after forming the sheath, and activating the entire particulate. The active material can be adhered on the sheath. However, it is also possible to add it to the sheath material so as to mix the sheath material before forming so that active material forms at least a part of the sheath.

When the active material of the core is different from the active material in and on the sheath, it is possible to form a catalyst and or adsorbant having dual functions.

Comparing with the conventional catalyst, it is thus possible to increase the range of temperatures, to decrease the steps of the reaction and to improve the selectivity in the application of the composition. Moreover, it is possible to form multilayered structures of the catalyst by using a plurality layers of active materials in the core and in the sheath and selecting the amount and type of the active material in each layer of the core or sheath for specialized functions.

When the other active material such as an adsorbing agent is used, or two or more different active materials such as an adsorbing agent and a catalyst are used, it is possible to prepare an active material-protecting structural composition having two or more functions.

The typical examples of the preparation of the active material-protecting structural composition of this invention will be illustrated in the appended examples.

The cores and layers of the active material for the cores and sheaths can be prepared by various processes.

For example, a mixture of the active material, an appropriate material of the combustible organic material, paste and water is formed into cores by extruding a mixture kneaded with water from an extruder and cut to size, or agglamerated or granulated by using a granulator, into spherical cores. A disc type granulator, or a rotary disc granulator is useful. A mixture of the active material and appropriate bonding materials may be tableted by a tableting machine or granulated, to form the granules of the active material for the core or otherwise mechanically subdivided.

A mixture of the active material and appropriate binders, fillers, carriers and diluent material is tableted by a tableting machine or is granulated, to form the grains of the active material for the core.

The cores of the active material are supplied to a granulator such as a plate-type granulator or a rotary disc-type granulator. The sheath material is coated on the cores, if necessary, under a water spray.

It is also possible to coat the cores with the sheath material by a compressing method or any convenient coating method.

As a special coating method, the cores of the active material are mixed in a slurry and the mixture is spray-dried. Any coating method can be used but coating by the plate-type granulator or the rotary disc-type granulator is preferred for forming uniformly thick sheaths.

When a combustible or vaporizable organic material such as cellulose saccharides, polyvinylalcohol naphthalene etc., is coated on the cores prior to the coating of the sheath material, it is possible to form a space between the sheath and the active material.

When the combustible or vaporizable organic material is mixed with the active material during formation of the core, it is possible to form a porous core. The formation of the pores in the core helps prevent breaks of the surrounding sheath due to volume changes of the core of the active material, and also effectively increases the surface area of the core of the active material.

The particles of core coated with the sheath material are heated to sinter the sheath material or binder. The combustible organic material simultaneously is burnt so as to form the structural composition having the structurally stable porous sheath having a plurality of communicating fine pores. The heating for sintering also serves to activate the active material when necessary. In the heating procedure the sheath material particles are dried at temperatures up to 200° C and then are gradually heated in a furnace. The rate of temperature increase is maintained at about the combustible temperature so as to completely burn off the combustible organic material, and the product is then further heated and kept at the final activating or sintering temperature for several hours. The sintering conditions are selected depending upon the composition required.

In order to activate certain types of active material, sometimes it is desirable to treat them in appropriate gas atmospheres such as nitrogen, hydrogen, etc., at the time of or after the formation of the sheath. When it is undesirable to contact the active material with a medium such as water, the cores are coated with saccharides as binders and then further coated with the sheath material and the saccharide is burnt off during the sintering of the sheath material.

Other appropriate conditions and procedures for forming the particles and sintering can be selected. For example, a catalyst composition may be prepared by granulating cores of a mixture of manganese dioxide and a ferric oxide and coating the cores with a mixture of alumina powder and a glass binder and then sintering the coated product to form the sheathed particles of this invention.

Such a catalyst composition is useful as an oxidation catalyst for oxidizing carbon monoxide and hydrocarbons in the exhaust gases of an internal combustion engine.

The examples of the functional material-protecting structural composition and the preparation thereof and the examples of a preparation of alkylphenols and an oxidation of hydrocarbon in an exhaust gas, are illustrated in detail in the appended examples. While the specific embodiment of the examples illustrate catalysts for the preparation of alkylphenols or the oxidation of hydrocarbons, the structurally strong particulate composition of this invention can also be prepared from mentioned or art recognized equivalent materials for other purposes.

EXAMPLE 1

100 parts of manganese oxide prepared by heating an electrolytic manganese dioxide at 1000° C and 5 parts of wheat starch and a small amount of water were mixed and kneaded. The mixture was supplied to a rotary disc type granulator and granulated by spraying water. The granules are further treated by the granulator by spraying water to form spherical tablets for the core having a predetermined size.

A sheathed material mixture was prepared by mixing and kneading 80 parts of fused alumina (120 mesh) and a binder of 15 parts of kaoline, 5 parts of feldspar, 5 parts of wheat starch and 20 parts of water. The tablets for the core were further treated by the granulator by spraying water and adding a coat of the sheath material mixture to a predetermined thickness. The coated products was dried at 80° – 120° C and was put in a vessel and was inserted in a furnace heated slowly to temperatures from 250° C to 600° C, and then further heated to 1200° C and there maintained for 3 hours so that the structural particulate composition of this invention having a stable sheath with many communicating pores was obtained.

The resulting active material-protecting structural composition has spherical shape with a core of manganese oxide of 5mm diameter, and a sheath of porous alumina having a thickness of 0.5 and 6.0 mm total diameter.

The physical properties of the composition were as follows:

The diameter and pore volume and apparent porosity of the sheath were measured after removing the core by crushing the sample. The same measurements were performed in the other examples.

| | |
|---|---|
| Compressive strength | 11.0 kg |
| Average pore diameter | 20 – 50 |
| Volume porosity of the sheath | 0.249 cc/g |
| Apparent porosity of sheath | 45.0% |

Phenol was reacted with methanol by using the particulate active material-protecting structural composition of this invention, in the following reaction conditions.

| | |
|---|---|
| phenol partial pressure | 0.0803 atm. |
| methanol partial pressure | 0.803 atm. |
| nitrogen partial pressure | 0.1164 atm. |
| space velocity (lhsv) | 442 hr$^{-1}$ |
| reaction temperature | 400° C |
| After 4 hours from the initiation of reaction: | |
| Conversion of phenol | 96.7% |
| Yield of 2,6-xylenol | 93.4% |
| Yield of 0-cresol | 3.3% |

A compressive strength of the structural composition after 50 hours in the reaction chamber, was 10.0 kg which was not decreased by the further exposure to the reaction. As it was clear, the structural composition had sufficient strength and activity in a practical use. When the manganese oxide was powdery it was not lost from the reaction.

COMPARISON EXAMPLE

Manganese oxide was granulated without a sheath, and was used in the same reaction scheme. The manganese oxide prepared by the heat treating in accordance with Example 1, was molded by a tableting machine to form cylinders of 5 mm and 5 mm of height, and were sintered at 1200° C. The resulting catalyst was used in the reaction of Example 1.

| After 5 hours from the initiation of reaction: | |
|---|---|
| Conversion of phenol | 98.5% |
| Yields of 2,6-xylenol | 86.0% |
| Yield of 0-cresol | 12.5% |
| Compressive strength | before reaction |
| of the catalyst | 25.9 kg |
| (per 5 cm of length) | after 50 hours reaction |
| | 0 kg |

The catalyst was powdery in the reaction, and it was troublesome to use in practical application.

However, in Example 1, the powdery catalyst was confined in the sheath and therefore was not lost. It was useful in practical application.

EXAMPLE 2

60 parts fused of alumina (120 mesh) and a binder of 40 parts of glass powder (400 mesh), 5 parts of wheat starch, 15 parts of water were mixed and kneaded to form the sheath material mixture. The core granules of Example 1 were supplied to the rotary disc type granulator and the sheath material was coated by spraying water and adding the sheath material. After coating the sheath material to a predetermined thickness, the coated product was dried at 80° – 120° C and was put in a vessel and was gradually heated in a furnace from 250° C to 600° C.

The product was kept at 750° C for 3 hours to sinter the product to form a stable sheath having many fine communicating holes.

The resulting active material-protecting structural composition had a spherical shape with powdery manganese oxide as the core and a sheath of porous alumina of 0.7 mm thickness and 6.4 mm diameter.

The resulting active material-protecting structural composition was used in the reaction of Example 1.

| After 4 hours form the initiation of reaction: | |
|---|---|
| Conversion of phenol | 82.3% |
| Yield of 2,6-xylenol | 75.1% |
| Yield of 0-cresol | 7.2% |
| Compressive strength | before reaction |
| of the composition | 10.4 kg |
| | after 50 hours reaction |
| | 8.0 kg |
| | after 100 hours reaction |
| | 8.0 kg |

The next example illustrates an application of the functional material-protecting composition of this invention as a catalytic composition for treating automobile exhaust gases. Various catalysts for treating an automobile exhaust gas especially for completely burning carbon monoxide and hydrocarbon in the exhaust gas, have been known. However, most of them are supported on a tangible porous carrier such as silica-alumina, α-alumina, etc. which carriers easily are crushed by vibration and abrasion, when used in automobile service. However, in accordance with the structurally strong compositions and methods of this invention, it is possible to solve the problem of crushing, because of the stable sheath of this invention.

EXAMPLE 3

An ammonia solution was added dropwise to an aqueous solution of a mixture of manganese nitrate and ferric nitrate to precipitate mixed gel and the mixture was dried and calcined at 500° C. It analyzed 45 parts of $Mn_2O_3$ and 55 parts of $Fe_2O_3$. 100 parts of the resulting mixture was mixed with 5 parts of cellulose acetate and a small amount of water and kneaded to form spherical core granules, in accordance with Example 1. These were used as cores.

A mixture of 60 parts of fused alumina (120 mesh), and a binder of 40 parts of lead borate-type glass powder (400 mesh pass), 5 parts of wheat starch, 15 parts of water was kneaded to form the sheath material. The core granules were supplied to the rotary disc-type granulator and the sheath material was coated thereon by spraying water and then adding the sheath material. After coating the sheath material to an appropriate thickness, the coated product was dried 80° – 120° C and was put in a vessel and gradually heated in a furnace from 200° C to 500° C. The product was kept at 500° C for 3 hours to sinter the product to form a stable sheath having many communicating micropores.

The resulting active material-protecting structural composition has a core part of $Mn_2O_3$ and $Fe_2O_3$ having 5 mm diameter and a sheath of alumina glass of 0.7 mm thickness.

The resulting active material-protecting structural composition was used for the oxidation of hexane as a test of complete oxidation of the exhaust gases of an internal combustion engine. The conditions of reaction are as follows.

hexane 1% ← air 99%

Space velocity ← 5000 hr$^{-1}$ 1 atm.

When the temperature of the catalyst bed reached at 155° C, the formation of carbon dioxide was initiated and 100% of hexane supplied at 230° C was converted to carbon dioxide.

A compressive strength of the catalyst composition was as follows:

| | |
|---|---|
| before reaction | 13.2 kg |
| after 50 hours reaction | 13.0 kg |

Even though the same reaction was intermittently preformed for 500 hours, no decrease of compressive strength was found. The catalyst composition was packed at the exhaust pipe of an automobile for 30 days running to a distance of 974 km. The compressive strength remained at 13.0 kg. The weight loss of total catalyst was low.

EXAMPLE 4

The following example described preparation of active structurally strong particulate compositions having space between the core and the sheath.

A mixture of 50 parts of walnut husk powder (100 mesh pass) 20 parts of wheat starch, 10 parts of corn starch and 30 parts of water was kneaded and coated on the core granules of Example 1 and then the granules were further coated with the sheath material of Example 1. The resulting three layered granules were put in a vessel and were heated in the manner set forth in Example 1, to obtain the active material-protecting structural composition having the functional material of the core having 5.5 mm diameter, a space of 0.23 mm thickness between the core and the sheath and a sheath of 0.64 mm thickness and 7.24 mmm of outer diameter.

The catalytic composition was used for the reaction of Example 1, at 400° C. The result was as follows:

| | |
|---|---|
| Conversion of phenol | 98.0% |
| Yield of 2,6-xylenol | 96.0% |
| Yield of 0-cresol | 2.0% |

EXAMPLE 5

The following example illustrates the improvement in reaction conversion and selectivity of the product by using the active material-protecting structural composition of this invention. In the reaction of phenol with methanol, o-cresol is first formed and then is converted to 2,6-xylenol. When the active material-protecting structural composition of this invention was used in the reaction, the selectivity for formation of 2,6-xylenol was improved.

It is presumed that phenol had access to the manganese oxide of of the core and was converted to o-cresol, and the resulting o-cresol was then further adsorbed into the core because of narrow passage of the sheath and slow diffusion therethrough so that the ratio of the conversion to form 2,6-xyleno was increased. When the size of the micropores of the sheath is decreased or the thickness of the sheath is increased, the reaction selectivity is further increased. This can be shown by the differences of the yield of 2,6-xylenol at the same conversion conditions of the phenol when the active material-protecting structural composition of this invention or the conventional catalyst was used. The effect was especially remarkable when the conversion was low.

In Example 2, the results were as follows:
Conversion of phenol of 82.3%
Yield of 2,6-xylenol of 71.5%
Yield of o-cresol of 7.2%
On the other hand, when the catalyst of manganese oxide of Reference Example 1 was used under the conditions of reaction temperature of 400° C, LHSV of 2.61 and MeOH/PhOH of 10 molar ratio, the results were as follows.
Conversion of phenol of 82.0%
Yield of 2,6-xylenol of 50%
Yield of o-cresol of 32%

EXAMPLE 6

In the following example, an alumina cement was used as the sheath material.

In accordance with Example 1, the manganese oxide core was prepared.

The core was covered with the mixture prepared by kneading 100 parts of alumina cement and 13 parts of water. The granules were left for 2 days in air to cure the alumina cement. The granules were put in a vessel and heated in a furnace by rising temperature to 620° C at a rate of about 100° C/hours and was kept at 620° C for 3 hours and was cooled in the furnace.

The resulting active material-protecting structural composition has a spherical shape and has powdery manganese oxide as the core and a sheath of porous alumina cement having 0.8 mm of thickness and 6.6 mm of diameter. The physical properties of the composition are as follows:

| | |
|---|---|
| Compressive strength | 15.7 kg |
| Diameter of fine holes of sheath | 500 – 1000 A |
| Volume of the fine holes of sheath | 0.152 cc/g |
| Apparent porosity of sheath | 46.4% |

The composition was used for the reaction in accordance with Example 1, at the reaction temperature of 410° C.

The following result was obtained:

| | |
|---|---|
| Conversion of phenol | 31% |
| Yield of 2,6-xylenol | 27% |
| Yield of o-cresol | 4% |

EXAMPLE 7

In the following example, a diatomaceous earth was used as the sheath material.

In accordance with Example 1, the core granules of manganese oxide were prepared. A mixture of 100 parts of diatomaceous earth and 70 parts of water was kneaded and coated on the granules of the core in accordance with Example 1, and the product was then dried at 80° – 120° C and was put in a vessel and heated in a furnace to 1000° C at a rate at about 100° C/hour and was kept at 1000° C for 3 hours and then the product was cooled in the furnace.

The resulting functional mterial-protecting structural composition was of spherical shape and had a manganese oxide core of 5 mm diameter and the sheath of 0.6 mm thickness made of diatomaceous earth.

The physical properties of the composition were as follows:

| | |
|---|---|
| Compressive strength | 4.0 kg |
| Diameter of the fine holes of sheath | 0.3 – 1.5μ |
| Volume of fine holes of sheath | 0.564 cc/g |
| Apparent porosity of sheath | 60.0% |

The composition was used for the reaction in accordance with Example 1, at the reaction temperature of 410° C.

The following result was obtained.

| | |
|---|---|
| Conversion of phenol | 90.0% |
| Yield of 2,6-xylenol | 83.0% |
| Yield of o-cresol | 7.0% |

EXAMPLE 8

In the following example, the sheath had communicating fine holes of relatively larger diameter.

In accordance with Example 1, manganese oxide cores were prepared.

A mixture of 85 parts fused of alumina (80 mesh) 12 parts of kaolin, 6 parts of feldspar, 5 parts of walnut husk powder (60 – 100 mesh) 5 parts of wheat starch, 3 parts of cellulose acetate and 10 parts of water were kneaded and coated on the core in accordance with Example 1. The product was dried at 80° – 120° C and was put in a vessel and was heated in a furnace to 1200° C at a rate of about 100° C/hour and was kept at 1200° C for 3 hours, and then the product was cooled in the furnace.

The resulting active material-protecting structural composition was of spherical shape and manganese oxide cores of 5 mm diameter and a sheath of 1.0 mm thickness of porous alumina.

The physical properties of the composition were as follows.

| | |
|---|---|
| Compressive strength | 14.3kg |
| Diameter of the fine holes of sheath | 80 – 120μ |
| Volume of fine holes of sheath | 0.25 cc/g |
| Apparent porosity of sheath | 42.0% |

The composition was used for the reaction in accordance with Example 1, at the reaction temperature of 410° C.

The following result was obtained.

| | |
|---|---|
| Conversion of phenol | 84.5% |
| Yield of 2,6-xylenol | 73.5% |
| Yield of o-cresol | 11.0% |

EXAMPLE 9

In the following example, copper metal powder was used as the sheath material.

In accordance with Example 1, manganese oxide cores were prepared.

A mixture of 100 parts of copper powder (80 –150 mesh), 3 parts of cellulose acetate, and 10 parts of water was kneaded and coated on the core in accordance with Example 1. The product was dried at 80° – 120° C and was put on a porcelain crucible (800 mm of diameter and 150 mm of depth and 5 mm of thickness) and was covered with a cap. The crucible and the cap were sealed with clay. After drying the clay, the crucible was heated in an electric furnace to 1000° C at a rate of about 100° C/hour and was kept at 1000° C for 3 hours, and the product was cooled in the furnace.

After cooling, the cap was removed and the product was washed with water and dried at 80° – 120° C.

The resulting active material-protecting structural composition was of spherical shape with manganese oxide cores having 5 mm diameter and a sheath of 0.8 mm thickness of porous copper.

The physical properties of the composition were as follows.

| | |
|---|---|
| Compressive strength | 27.30 kg |
| Diameter of fine holes of sheath | 3 – 6μ |
| Volume of fine holes of sheath | 0.078 cc/g |

-continued

| | |
|---|---|
| Apparent porosity of sheath | 36.8% |

The composition was used for the reaction in accordance with Example 1, at the reaction temperature of 450° C.

The following result was obtained.

| | |
|---|---|
| Conversion of phenol | 39% |
| Yield of 2,6-xylenol | 16% |
| Yield of o-cresol | 23% |

What we claim is:

1. A structurally strong particulate composite of active materials comprising a core and a microporous sheath surrounding said core, said core containing the active material selected from group consisting of catalysts, adsorbants, microsieves, ion exchangers or mixtures thereof in particulate form and said microporous sheath consisting of a solid, strengthening, enclosing structure for said core having an open porous structure including communicating open pores forming passageways for access to said core from the space surrounding said sheathed composite, said porous structure resulting from sintering a sheath-forming material admixed with an organic material that is combustible at sintering temperatures, said sheath-forming material being a crystalline or amorphous inorganic salt or oxide selected from the group consisting of fused alumina, silicon carbide, alumina, silica, zirconia, feldspar, sodium glass, lead glass, borosilicate glass, Portland cement and amorphous alumina cements and said communicating open pores resulting from the combustion of said combustible organic material thereby providing voids comprising said passageways for access to said core from the space surrounding said particulate composite.

2. The particulate composition according to claim 1 wherein said core of active material is separated from said surrounding sheath by an open space whereby volume changes of said active material do not disrupt the continuity of said surrounding sheath.

3. The composite according to claim 1 wherein said microporous sheath material includes a further active material.

4. The composite according to claim 1 wherein said active material is thermally activated.

5. The composite according to claim 1 wherein said particulate cores comprise a plurality of layers, each layer comprising an active material which may be the same or different from said other layers.

6. The particulate composite according to claim 1 wherein said strengthening structure of said microporous sheath has a crush strength greater than 3 kg Kiya Hardness Test and wherein the thickness of said sheath is in the range of 5 to 100% of the inside diameter of said sheath.

7. The particulate composite according to claim 1 wherein said microporous sheath has pore sizes in the range 0.05 to 100μ, an apparent porosity in the range 20 - 70% and a pore volume in the range 0.01 to 0.7 cc/gm.

8. The composition according to claim 1 wherein said active material is manganese dioxide catalyst.

9. The process for the preparing particulate composites according to claim 1 wherein said active materials are enclosed by a structurally stronger sheath which comprises the steps of a) shaping individual cores comprising said active material in particulate form, b) coating said cores with a coating composition of sheath-forming material comprising (1) a structural component of crystalline and amorphous inorganic oxides, salts and mixtures thereof selected from the group consisting of fused alumina, silicon carbide, alumina, silica, zirconia, feldspar, sodium glass, lead glass, borasilicate glass, Portland cement, amorphous alumina cements; (2) a binder component for binding said structural component; and (3) a fugitive component, said fugitive component being selected from among organic compounds which are combustible at sintering temperatures; c) then forming said coat into a microporous sheath by heating, said coated cores to elevated sintering temperatures thus sintering said coat on said cores, and combusting said fugitive material during said heating step to concurrently form pores in the voids previously occupied by said fugitive component.

10. The process according to claim 9 wherein said individual cores are formed by the process of granulation, tableting or mechanical subdivision.

11. The method according to claim 9 for preparing a catalyst for methylating phenols which comprises the steps of granulating manganese oxide to size, with a binder, to form a core, coating said core with a sheath-forming coating material and said sheath-forming material being a crystalline or amorphous inorganic salt or oxide selected from the group consisting of fused alumina, silicon carbide, alumina, silica, zirconia, feldspar, sodium glass, lead glass, borosilicate glass, Portland cement and amorphous alumina cements and sufficient water to form said coating mixture, drying said coating and then heating said coated composite to sintering temperature to form the particulate composite of a core coated with a sintered microporous sheath.

12. The process according to claim 9 wherein said active material is a manganese dioxide catalyst.

13. The process for preparing particulate composites wherein said active materials are enclosed by a structurally stronger sheath which comprises the steps of
  a. shaping individual cores comprising said active material in particulate form,
  b. coating the cores in the first coat of fugitive material
  c. further coating said cores with a second coat of a coating composition of sheath-forming material comprising
     1. a structural component of crystalline and amorphous inorganic oxides, salts and mixtures thereof selected from the group consisting of fused alumina, silicon carbide, alumina, silica, zirconia, feldspar, sodium glass, lead glass, borosilicate glass, Portland cement, amorphous alumina cements;
     2. a binder for said composition component; and
     3. a fugitive component, said fugitive component being selected from among material which are combustible at sintering temperatures;
  d. then forming said second coat into a microporous sheath by heating said coated cores to elevated sintering temperatures thus sintering said second coat around said cores, and also combusting said fugitive material from said first and second coats during said heating step to concurrently form voids in the spaces previously occupied by said fugitive component.

* * * * *